United States Patent [19]

Miwa et al.

[11] Patent Number: 4,778,762
[45] Date of Patent: * Oct. 18, 1988

[54] PLASMID

[75] Inventors: Kiyoshi Miwa, Matsudo; Mahito Terabe; Takayasu Tsuchida, both of Yokohama; Masaaki Ishida, Kawasaki; Shigeru Nakamori, Yokohama; Konosuke Sano, Tokyo, all of Japan; Haruo Momose, East Lansing, Mich.

[73] Assignee: Ajinomoto Company Incorporated, Tokyo, Japan

[*] Notice: The portion of the term of this patent subsequent to Jan. 24, 2001 has been disclaimed.

[21] Appl. No.: 434,853

[22] Filed: Oct. 18, 1982

Related U.S. Application Data

[63] Continuation-in-part of Ser. No. 255,169, Apr. 17, 1981, Pat. No. 4,427,773, and a continuation-in-part of Ser. No. 261,557, May 7, 1981, Pat. No. 4,560,654.

[30] Foreign Application Priority Data

Apr. 17, 1980 [JP] Japan .................................. 55-51001
May 16, 1980 [JP] Japan .................................. 55-65007

[51] Int. Cl.[4] ...................... C12N 15/00; C12N 1/20; C12P 21/00; C12P 21/02; C12P 19/34; C12R 1/13; C12R 1/15
[52] U.S. Cl. ..................................... 435/320; 435/68; 435/70; 435/91; 435/172.3; 435/253; 435/840; 435/843; 935/29; 935/72
[58] Field of Search ...................... 435/68, 70, 91, 172, 435/253, 317, 840, 843, 844, 845, 846, 172.1, 317.1, 326; 935/29, 72-75

[56] References Cited

U.S. PATENT DOCUMENTS

| 4,427,773 | 1/1984 | Tsuchida et al. | 435/110 |
| 4,442,208 | 4/1984 | Tsuchida et al. | 935/72 |
| 4,452,890 | 6/1984 | Tsuchida et al. | 435/172.3 |
| 4,514,502 | 4/1985 | Miwa et al. | 435/172.3 |
| 4,601,983 | 7/1986 | Nakamori et al. | 435/115 |

FOREIGN PATENT DOCUMENTS 0058889 1/1982 European Pat. Off. ............. 435/91

OTHER PUBLICATIONS

Tsuchida et al.: Chem. Abstr., 96:102492m, (1982).
Gross et al.: J. Gen. Microbiol., 115, 479, (1979).
Schiller et al.: Antimicrob. Agents Chemother., 18, 814, (1980).
Kaneko et al.: Chem. Abstr., 91:35517e, (1979), of Agric. Biol. Chem., 43, 867, (1979).
Helling et al.: in *Genetic Engineering*, Chakrabarty (ed.), CRC Press, 1978, pp. 9-14.
Miwa et al.: Chem. Abtr., 96:120894y, (1982).

*Primary Examiner*—James Martinell
*Attorney, Agent, or Firm*—Oblon, Fisher, Spivak, McClelland & Maier

[57] ABSTRACT

A substantially pure plasmid which is characterized by a molecular weight of 3.0±0.1 megadalton and the restriction endonuclease-cleavage map shown in the Figure. This plasmid is capable of propagating in Corynebacteria and due to its size is useful as a vector for the cloning of exogenous genes.

5 Claims, 1 Drawing Sheet

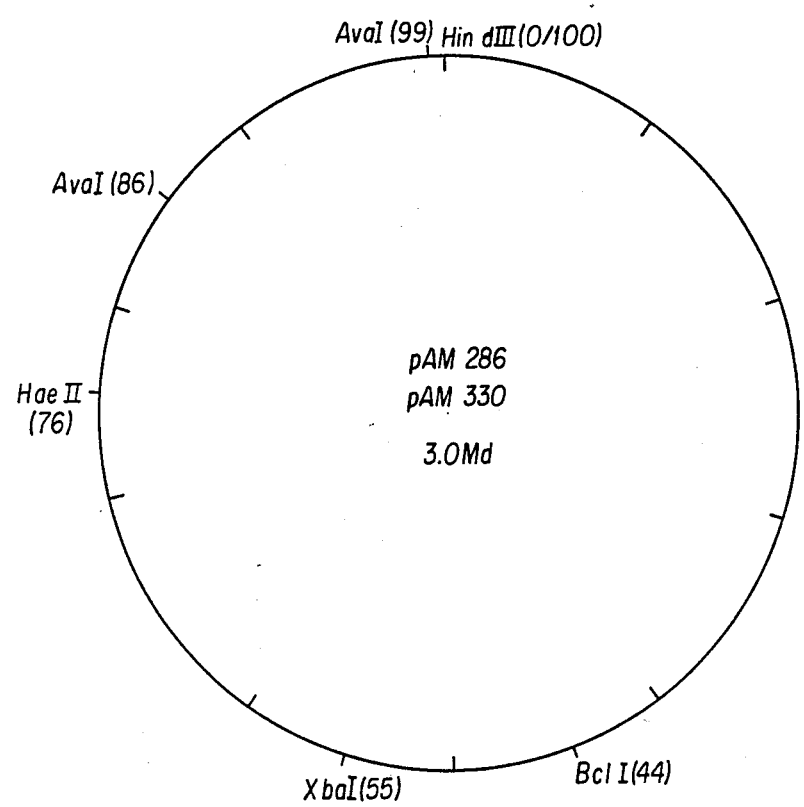

PLASMID

This application is a continuation-in-part of Ser. No. 255,169, filed Apr. 17, 1981 now U.S. Pat. No. 4,427,773 issued Jan. 24, 1984 and a continuation-in-part of Ser. No. 261,557, filed May 7, 1981 now U.S. Pat. No. 4,560,654 issued Dec. 24, 1985.

BACKGROUND OF THE INVENTION

1. Field of the Invention

The present invention relates to a plasmid, and particularly to a plasmid capable of propagating in Coryneform glutamic acid-producing bacteria.

2. Description of the Prior Art

Coryneform glutamic acid producing bacteria, so-called "Coryneform bacteria", are known to produce substantial amounts of L-glutamic acid, and mutants of the Coryneform glutamic acid producing bacteria produce amino acids such as lysine and purine nucleotides such as inosinic acid. Therefore, they are of great importance to the fermentation industry.

The recently developed gene splicing techniques can successfully be applied to the breeding or improving of industrial microorganisms, especially in the case of *Escherichia coli*. It has been difficult, however, to apply gene splicing techniques for the breeding or improving of industrial microorganisms or the like of Coryneform glutamic acid-producing bacteria, since suitable plasmids useful for the construction of such industrially useful Coryneform glutamic acid producing bacteria have not yet been developed.

Although a plasmid capable of propagating in Coryneform glutamic acid-producing bacteria was reported in *Agric. Biol. Chem.*, 43, 867, (1979), the molecular weight of the known plasmid is 37 megadalton and is too large and inconvenient to use for construction of industrial microorganisms of Coryneform bacteria by gene splicing techniques.

A need, therefore, continues to exist for the development of a novel plasmid useful for the breeding or improving of industrial microorganisms of Coryneform glutamic acid-producing bacteria.

SUMMARY OF THE INVENTION

Accordingly, one object of the present invention is to provide a plasmid useful for the breeding or improving of industrially useful Coryneform glutamic acid-producing bacteria.

Briefly, this and other objects of the present invention, as will hereinafter become readily apparent, can be attained by providing an essentially pure plasmid which is characterized by a molecular weight of $3.0 \pm 0.1$ megadalton and a restriction endonuclease cleavage map as shown in the FIGURE.

BRIEF DESCRIPTION OF THE DRAWING

A more complete appreciation of the invention and many of the attendant advantages thereof will be readily obtained as the same becomes better understood by reference to the following detailed descrition when considered in connection with the accompanying drawing, wherein:

the FIGURE is the restriction endonuclease cleavage map of the plasmids pAM 330 and pAM 286.

DETAILED DESCRIPTION OF THE PREFERRED EMBODIMENTS

Specimens of the plasmid of the present invention are pAM 330 which is separated from *Brevibacterium lactofermentum* ATCC 13869, and pAM 286 separated from *Corynebacterium glutamicum* AJ 11560 (FERM-P 5485). These plasmids have the following common characteristics:

The molecular weights of the plasmids calculated by their migration distance on agarose gel electrophoresis and the length of their DNA-chains under an electron microscope are both 3.0 megadalton. The sensitivity to restriction enzymes and the restriction map of each plasmid are the same as shown in Table 1 and in the FIGURE, respectively.

The plasmids pAM 330 and pAM 286 can be obtained from the cells of the deposited microorganisms *Brevibacterium lactofernemtum* ATCC 13869 and *Corynebacterium glutamicum* FERM-P 5485 (NRRLB-12415), respectively, by lysing the cells previously harvested at a late exponential growth phase by lysozyme and SDS, adding polyethylene glycol to a supernatant obtained from the lysate by centrifugation at 30,000 xg, and purifying the precipitated DNA by fractionation using cesium chloride-ethidium bromide equilibrium density gradient centrifugation.

TABLE 1

| Restriction Enzyme | | Number of Restriction Sites |
|---|---|---|
| Alu I | *Arthrobacter luteus* | >4 |
| Ava I | *Anabena variabilis* | >2 |
| Bcl I | *Bacillus caldolyticus* | 1 |
| BamH I | *Bacillus amyloliquefaciens* H | 0 |
| Bgl II | *Bacillus globigii* | 0 |
| BstE II | *Bacillus stearothermophilus* ET | >4 |
| EcoR I | *Escherichia coli* RI+ | 0 |
| Hae II | *Haemophilus aegyptius* | 1 |
| HgiA I | *Herpetosiphon giganteus* | >4 |
| Hind II | *Haemophilus influenzae* | >4 |
| Hind III | *Haemophilus influenzae* | 1 |
| Hpa II | *Haemophilus parainfluenzae* | >4 |
| Kpn I | *Klebsiella pneumoniae* | 0 |
| Pvu II | *Proteus vulgaris* | 0 |
| Sac I | *Streptomyces achromogenes* | 0 |
| Sal I | *Streptomyces albus* | 0 |
| Sau 3A | *Staphylococcus aureus* | >4 |
| Sma I | *Serratia marcescens* | 1 |
| Sst I | *Streptomyces stanford* | 0 |
| Xba I | *Xanthomonas badrii* | 1 |
| Xho I | *Xanthomonas holicola* | 1 |
| Xma I | *Xanthomonas malvacearum* | 1 |
| Xor II | *Xanthomonas oryzae* | 0 |

Coryneform bacteria are aerobic, gram-positive rods, non-spolutating, and non-acidfast, and are described in Bergey's Manual of Determinative Bacteriology, 8th ed., 599, (1974). Examples of wild strains of Coryneform glutamic acid-producing bacteria useful as hosts in this invention are as follows:

*Brevibacterium divaricatum* ATCC 14020,
*Brevibacterium saccharoliticum* ATCC 14066,
*Brevibacterium immariophilum* ATCC 14068,
*Brevibacterium lactofermentum* ATCC 13869,
*Brevibacterium roseum* ATCC 13825,
*Brevibacterium flavum* ATCC 13826,
*Brevibacterium thiogenitalis* ATCC 19240,
*Corynebacterium acetoacidophilum* ATCC 13870,
*Corynebacterium acetoglutamicum* ATCC 15806,
*Corynebacterium callunae* ATCC 15991,

*Corynebacterium glutamicum* ATCC 13032, 13060,
*Corynebacterium lilium* ATCC 15990,
*Corynebacterium melassecola* ATCC 17965,
*Microbacterium ammoniaphilum* ATCC 15354.

Coryneform glutamic acid-producing bacteria also include mutants which have lost the ability to produce glutamic acid or are capable of producing other amino acids such as lysine and arginine; purine nucleosides such as inosine; purine nucleotides such as inosine-5'-monophosphate; and other fermentation products.

In the cells of Coryneform glutamic acid-producing bacteria, the plasmids of the present invention are stably maintained. Since the plasmids of the present invention can propagate in cells of Coryneform glutamic acid-producing bacteria, the information of a foreign gene inserted in the plasmid can be amplified in the hosts.

The incorporation of plasmid DNA into the hosts of Coryneform glutamic acid-producing bacteria can be done by treating the cells of the DNA-recipient with calcium chloride to increase the permeability of DNA, as is reported regarding *E. coli* K-12 (Mandel, M and Higa, A., *J. Mol. Biol.*, 53, 159 (1970), or by incorporation into the host at a specific stage of growth when the cells become capable of incorporating DNA therein (competent cells) as is reported in *Bacillus subtilis* (Duncan, C. H., Wilson, G. A., and Young, F. E., *Gene* 1, 153 (1977)).

The plasmid can also be incorporated into the DNA-recipient by forming protoplasts or spheroplasts of the DNA-recipient which easily incorporate plasmid DNA therein, as is known in *Bacillus subtilis*, actinomycetes and yeast (Chang, S. and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Nat'l Acad. Sci.*, U.S.A. 75, 1929 (1978)).

A foreign gene can be inserted into the plasmid of the present invention at the positions cleaved by the restriction enzymes shown in Table 1 and more preferably at the cleavage position which number is one. Genomic DNA of Coryneform glutamic acid-producing bacteria is the most preferred of the foreign genes. A preferred vector can be obtained from the present plasmid by removing all or a part of the DNA regions other than the drive unit, since the molecular weight becomes small. The copy number of the present plasmid is sufficiently large and therefore is suitable for amplifying foreign genes.

Having generally described this invention, a further understanding can be obtained by reference to certain specific examples which are provided herein for purposes of illustration only and are not intended to be limiting unless otherwise specified.

EXAMPLE 1

Preparation of pAM 330 DNA

*Brevibacterium lactofermentum* ATCC 13869 which possessed pAM 330 was cultured at 30° C. in CMG medium at pH 7.2 containing 1 g/dl peptone, 1 g/dl yeast extract, 0.5 g/dl glucose and 0.5 g/dl NaCl until the late exponential growth phase was reached. Cells were harvested and lysed by treatment with lysozyme and SDS. The lysate was centrifuged to obtain a supernatant, which was added to polyethylene glycol, and the resulting mixture was evaporated to precipitate DNA. The precipitate was dissolved in Tris-EDTA-NaCl buffer at pH 8.0, and the solution was subjected to agarose-gel electrophoresis (5 v/cm, 15 hours). Thus, 74 μg of pAM 330 plasmid DNA wa obtained.

Molecular weight of PAM 330

The molecular weight of pAM 330 was calculated by its migration distance upon electrophoresis on agarose gel and by the length of its DNA-chain as determined under an electron microscope. Agarose gel electrophoresis was conducted by the method of P. A. Sharp, (*Biochemistry* 12, 3055 (1973)), (0.7–0.8% gel, 5 v/cm, and 15 hours). The molecular weight was calculated based on the mobility differences of pBR 322 (Boliver F. et al; *Gene* 2, 95, (1977)), pUB 110 (Gryczan, T. J. et al; *J. Bacteriol.*, 134, 318, 1978)) and Col $E_1$ (Bazaral, M. et al; *J. Mol. Biol.*, 36, 185, 1968)).

The cytochrome C monolayer method described by Kleinschmidt, A. and Zahn, R. K. in *Z. Naturforsh*, 14b 770 (1959) was used for the electron microscope observation.

Agarose-gel electrophoresis of digested plasmid

Commercially available restriction enzymes sold by Bethesda Research Laboratory Co., Boehringer Mannheim Co., New England Biolab Co., Worthington Biochemical Co. were used. Digestion by restriction enzyme was carried out using an excessive amount of restriction enzyme, e.g. more than 3 times the amount required. The digestion reaction was carried out according to the directions by the distributors. When digestion was done using more than two restriction enzymes, DNA fragments formed by the last digestion reaction were separated by the method described by T. Tanaka, and B. Weisblum in *J. Bacteriol.*, 121, 354 (1975) and precipitated by ethanol. Thereafter, the separated DNA fractions were subjected to the following digestion reaction.

The DNA fragments were thereafter subjected to agarose-gel electrophoresis. The agarose concentration was 0.7 to 1%, the voltage was 5 to 20 v and electrophoresis was continued for 1 to 3 hours. The molecular weight was calculated based on the mobility difference between the DNA fragments and authentic samples of φ X 174 RF-Hae III fragment and λ DNA-Hind III fragment both produced and sold by Bethesda Research Laboratory.

Determination of copy number of pAM 330

*Brevibacterium lactofermentum* ATCC 13869 containing pAM 330 was cultured at 30° C. overnight in 5 ml of a minimal medium at pH 7.0 containing per liter, 20 g glucose, 10 g $(NH_4)_2SO_4$, 2.5 g urea, 1 g $KH_2PO_4$, 0.4 g $MgSO_4.7H_2O$), 50 μg biotin, 200 μg thiamine.HCl, 0.01 g $FeSO_4.7HH_2O$ and 0.01 g $MnSO_4.4H_2O$, and further containing 100 μCi of $^3H$-thymidine. The cells obtained were lysed by lysozyme and SDS, and a circular plasmid was separated by cesium chloride-ethidium bromide equilibrium density gradient centrifugation.

The radioactivity recovery in the circular plasmid was 0.8 to 1.0%. Since the molecular weight of pAM 330 was $3 \times 10^6$ and that of chromosomal DNA (ATCC 13869) was $3 \times 10^9$, the copy number of the circular plasmid was calculated as 8 to 10. (Only a circular plasmid can be determined by the method above and plasmids in cells and plasmids which became linear are not included. Therefore, the actual copy number may be larger than that determined (Kenju Nagahari; BUNSHI IKUSHU TO OHYOBISEIBUTSU, Kodansha, p172, (1979)).

Preparation of recombinant DNA from pAM 330

*Brevibacterium lactofermentum* No. 5116 (NRRL B-12405), a mutant sensitive to high temperature and induced from strain No. 2256 (ATCC 13869), was cultured at 30° C. for 3 hours with shaking in 1 l of CMG-medium containing 1 g/dl peptone, 1 g/dl yeast extract, 0.5 g/dl glucose and 0.5 g/dl NaCl (the pH was adjusted to 7.2), and bacterial cells in the exponential growth phase were harvested. Chromosomal DNA was extracted by a conventional phenol-method, and 3.5 mg of purified DNA was obtained.

Ten µg samples of the chromosomal DNA were treated with the restriction endonucleases Hind III at 37° C. for 10, 30 and 60 minutes respectively, to cleave DNA chains, and then each sample was heated at 65° C. for 5 minutes. Five µg of pAM 330 DNA was also treated with Hind III at 37° C. for 1 hour to cleave the DNA completely, and then was heated at 65° C. for 5 minutes.

The digested chromosomal DNA solution and the cleaved vector DNA solution were mixed and subjected to a ligation reaction of the DNA fragments by a T4 phage DNA-ligase in the presence of ATP and dithiothreitol at 10° C. for 24 hours. The reaction mixture was then heated at 65° C. for 5 minutes, and two fold volumes of ethanol were added to it. The recombinant DNA which precipitated was recovered.

Glutamic acid requiring strains of *Brevibacterium lactofermentum* No. 3 (NRRL B-12406), which were derived from *Brevibacterium lactofermentum* No. 5116 by N-methyl-N'-nitro-N-nitrosoguanidine mutagenesis, were cultured in 20 ml of CMG at 30° C. with shaking. Cells in the exponential growth phase were harvested, and suspended in a 0.1M MgCl$_2$ solution and then in a 0.1M CaCl$_2$ solution in an ice-bath, whereby, "competent" cells having the ability of DNA uptake were prepared.

Into the competent cell suspension, the recombinant DNA was added. The suspension was kept in an ice-bath for 30 minutes, then heated at 42° C. for 2 minutes, and again allowed to stand in an ice-bath for 30 minutes. The cells, thus containing the hybrid plasmid DNA, were inoculated into an L-medium and the medium was shaken at 37° C. for 3 hours, whereby the transformation reaction was completed. The cells were harvested, washed, and resuspended. A small portion of the cell suspension was spread on an agar plate containing, 20 g glucose, 10 g (NH$_4$)$_2$SO$_4$, 2.5 g urea, 1 g KH$_2$PO$_4$, 0.4 g MgSO$_4$.7H$_2$O, 50 µg biotin, 200 µg thiamine hydrochloride, 0.01 g FeSO$_4$.7H$_2$O, 0.01 g MnSO$_4$.4H$_2$O and 20 g agar, per liter, (pH was adjusted to 7.2). The plate was incubated at 37° C. After 4 days incubation, all of the colonies which appeared were picked up, purified and isolated.

Strains which became capable of producing L-glutamic acid by the transformation reaction were picked up as the transformants. Among the transformants, the greatest L-glutamic acid producer AJ 11561 (FERM-P 5469) (NRRL B-12408) was selected.

L-Glutamic acid productivity of AJ 11561 was tested in comparison to the DNA-donor and the recipients, as follows:

The fermentation medium contained 3.6 g/dl glucose, 0.5 g/dl urea, 0.1 g KH$_2$PO$_4$, 0.1 g/dl MgSO$_4$.7H$_2$O, 3 ml/dl soybean hydrolysate ("Mieki"), 100 µg/l thiamine. HCl 3 µg/l biotin, 1 mg/dl FeSO$_4$.7H$_2$O, 1 mg/dl MnSO$_4$.H$_2$O and 2.5 g/dl CaCO$_3$ (separately sterilized) and the pH was adjusted to 7.0.

Twenty ml of the fermentation medium was placed in a 500 ml flask. The medium was inoculated with one loopful inoculum of the test microorganisms and cultivation was performed at 31° C. for 48 hours.

The amounts of L-glutamic acid in the supernatant of the fermentation broth were determined by enzymatic assay.

TABLE 1

| Microorganisms tested | Amounts of L-glutamic acid accumulated (mg/dl) |
|---|---|
| *Brevibacterium lactofermentum* No. 5116 | 550 |
| *Brevibacterium lactofermentum* No. 3 | 0 |
| *Brevibacterium lactofermentum* AJ 11561 | 980 |

EXAMPLE 2

(1) Preparation of chromosomal DNA possessing genetic information relating to L-glutamic acid production

*Corynebacterium glutamicum* No. 5707 (NRRLB-12410), a mutant resistant to ketomalonic acid and induced from *Corynebacterium glutamicum* AJ 11560 (FERM-P 5485) (NRRL B-12415), was cultured at 30° C. for 3 hours with shaking in 1 l of CMG-medium containing 1 g/dl peptone, 1 g/dl yeast extract, 0.5 g/dl glucose and 0.5 g/dl NaCl (pH was adjusted to 7.2), and bacterial cells in the exponential growth phase were harvested. Chromosomal DNA was extracted by a conventional phenol-method, and 4.0 mg of purified DNA was obtained.

*Corynebacterium glutamicum* AFJ 11560 was newly isolated as a suitable strain for the purpose of this invention.

This strain, AJ 11560, was classified in section III of genus Corynebacterium described in Bergey's Manual of Determinative Bacteriology (8th edition, 1974). However, the taxonomic characteristics of the species belonging to section III are not disclosed in the Manual. Only names of species are disclosed in section III. Therefore, all original reports disclosed in the Manual as to section III are referred to. AJ 11560 was identified with *Corynebacterium glutamicum* described in "Bull. Agr. Chem. Soc. Japan, 22 176~185 (1958)" and "J. Gen. Appl. Microbiol., 13, 279~301 (1967)".

(2) Preparation of vector DNA

As the vector, the DNA of plasmid pAM286 (M.W. 3×10$^6$ dalton) was prepared as follows:

A strain of *Corynebacterium glutamicum* AJ 11560 harboring the plasmid pAM 286 was incubated at 30° C. in 1 l of CMG-medium. After the strain was incubated until the late log phase, the cells were harvested and then lysed by treatment with lysozyme and SDS. The lysate was centrifuged at 30,000 xg for 30 minutes to obtain a supernatant. After concentrating the supernatant, 60 µg of the plasmid DNA was obtained by fractionation using agarose gel electrophoresis. (3) Insertion of chromosomal DNA fragment into vector Ten µg samples of the chromosomal DNA were treated with each of the restriction endonucleases Hind III and Xma I at 37° C. for 10, 30 and 60 minutes respectively, to cleave DNA chains, and then the samples were heated at 65° C. for 5 minutes. Ten μg of the vector DNA was also treated with each of the restriction endonucleases, Hind III and Xma I at 37° C. for 1 hour to cleave the DNA completely, and then was heated at 65° C. for 5 minutes.

The digested chromosomal DNA solution and the cleaved vector DNA solution were mixed and subjected to a ligation reaction of the DNA fragments by a T4 phage DNA-ligase in the presence of ATP and dithiothreitol at 10° C. for 24 hours. The reaction mixture was then heated at 65° C. for 5 minutes, and two fold volumes of ethanol were added to it. The recombinant DNA which precipitated was recovered.

(4) Genetic transformation with the hybrid plasmid harboring the genetic information related to glutamic acid production L-Glutamic acid requiring strains of *Corynebacterium glutamicum* No. 12 (NRRL B-12411) and No. 26 (NRRL B-12412), which were derived from *Corynebacterium glutamicum* No. 5707 by N-methyl-N'-nitro-N-nitrosoguanidine mutagenesis, were cultured in 20 ml of CMG-medium at 30° C. with shaking. Cells in the exponential growth phase were harvested, and suspended in a 0.1 M MgCl$_2$ solution and then in a 0.1 M CaCl$_2$ solution in an ice-bath, whereby, "competent" cells having the ability of DNA uptake were prepared.

Into the competent cell suspension, the DNA obtained in step (3), which contains the hybrid plasmid DNA, was added. The suspension was kept in an ice-bath for 30 minutes, then heated at 42° C. for 2 minutes, and again allowed to stand in an ice-bath for 30 minutes. The cells, thus containing the hybrid plasmid DNA, were inoculated into an L-medium and the medium was shaken at 37° C. for 3 hours, whereby the transformation reaction was completed. The cells were harvested, washed, and resuspended. The reaction mixture, after having been diluted, of the cell suspension was spread on an agar plate containing 20 g glucose, 10 g (NH$_4$)$_2$SO$_4$, 2.5 g urea, 1 g KH$_2$PO$_4$, 0.4 g MgSO$_4$.7H$_2$O, 50 μg biotin, 20 μg thiamine hydrochloride, 0.01 g FeSO$_4$.7H$_2$O, 0.01 g MnSO$_4$.4H$_2$O and 20 g agar, per liter, (pH was adjusted to 7.0). The plate was incubated at 37° C. After 4 days incubation, all of the colonies which appeared were picked up, purified and isolated.

AJ 11566 (FERM-P 5486) (NRRL B-12413) from the recipient strain No. 12 using Hind III, and AJ 11567 (FERM-P 5487) (NRRL B-12414) was obtained from the recipient strain No. 26 using Xma I.

(5) Production of L-glutamic acid by the prepared glutamic acid producing strain The transformants obtained in step (4) were cultured to test their L-glutamic acid productivity. The DNA-donor strain No. 5707 and the recipients strains were cultured in the same manner for comparison.

The culture medium contained 3.6 g/dl glucose, 0.5 g/dl urea, 0.1 g KH$_2$PO$_4$, 0.1 g/dl MgSO$_4$.7H$_2$O, 3 ml/dl soybean hydrolysate ("Mieki"), 100 μg/l thiamine.HCl, 3 μg/l biotin, 1 mg/dl FeSO$_4$.7H$_2$O, 1 mg/dl MnSO$_4$.4H$_2$O and 2.5 g/dl CaCO$_3$ (separately sterilized) and the pH was adjusted to 7.0.

Twenty ml of the fermentation medium was placed in a 500 ml flask. The medium was inoculated with one inoculum loopful of the test microorganisms, and the cultivation was performed at 31° C. for 48 hours.

The amounts of L-glutamic acid in the supernatant of the fermentation broth were determined by enzymatic assay.

TABLE 2

| Microorganisms tested | Amounts of L-glutamic acid accumulated (mg/dl) |
|---|---|
| *Corynebacterium glutamicum* No. 5707 | 600 |
| *Corynebacterium glutamicum* No. 12 | 0 |
| *Corynebacterium glutamicum* No. 26 | 0 |
| *Corynebacterium glutamicum* AJ 11566 | 1010 |
| *Corynebacterium glutamicum* AJ 11567 | 1000 |

EXAMPLE 3

Preparation of pAM 286 DNA

*Corynebacterium glutamicum* AJ 11560 (FERM-P 5485) which contains pAM 286 DNA was cultured in CMG medium at 30° C. until the late exponential growth phase. The cells harvested were lysed by lysozyme and SDS treatment. The lysate supernatant was separated by centrifugation at 300,000 xg for 30 minutes, to which was added polyethyleneglycol which resulted in the precipitation of DNA. The precipitate was dissolved in 1/10 volume of TEN buffer at pH 8.0 containing 20 mM Tris, 20 mM NaCl and 1 mM of EDTA, and thereafter circular plasmid was separated by cesium chloride-ethidium bromide equilibrium density gradient centrifugation. Ethidium bromide was removed from the circular plasmid fraction which was thereafter subjected to dialysis purification, whereby 82 μg of pAM 286 DNA was obtained. The above plasmid DNA isolation procedure conformed to the disclosure by Tamio Yamakawa (ed.) in SEIKAGAKU JIKKEN KOZA Vol. 1, (1) 73, Tokyo Kagaku Donin (1975).

Digestion with restriction enzyme and agarose-gel electrophoresis were performed following the procedure shown in Example 1.

Determination of the copy number of pAM 286 was carried out in the same manner shown in Example 1 using *Corynebacterium glutamicum* AJ 11560 as the host, and the copy number was 8 to 10.

Determination of molecular weight of pAM 286

The molecular weight of pAM 286 was determined by agarose-gel electrophoresis and electron microscope observation as described in Example 1.

Preparation of recombinant DNA from pAM 286

*Corynebacterium glutamicum* NO. 22 (NRRL B-12416), a mutant resistant to S-(2-aminoethyl)-cystein (AEC) and induced from *Corynebacterium glutamicum* AJ 11560 (FERM-P 5485) (NRRL B-12415), was cultured at 30° C. for 3 hours with shaking in 1 l of CMG-medium containing 1 g/dl peptone, 1 g/dl yeast extract, 0.5 g/dl glucose and 0.5 g/dl NaCl (pH was adjusted to 7.2), and bacterial cells in the exponential growth phase were harvested. Chromosomal DNA was extracted by a conventional phenol-method, and 4.0 mg of purified DNA was obtained.

Ten μg samples of the chromosomal DNA were treated with the restriction endonuclease XbaI at 37° C. for 10, 30 and 60 minutes, respectively to cleave DNA chains, and then each sample was heated at 65° C. for 5 minutes. Five μg of the vector DNA was also treated with the restriction endonuclease, XbaI at 37° C. for 1 hour to cleave the DNA completely, and then was heated at 65° C. for 5 minutes.

The digested chromosomal and vector DNAs were mixed and subjected to the ligation reaction by T4 DNA-ligase in the presence of ATP and dithiothreitol at 10° C. for 24 hours. The reaction mixture was then heated at 65° C. for 5 minutes, and two fold volumes of ethanol were added to it. The recombinant DNA which precipitated was recovered.

An L-lysine requiring strain, *Corynebacterium glutamicum* No. 97 (NRRL B-12417), which was derived from *Corynebacterium glutamicum* No. 22 by N-methyl-N'-nitro-N-nitrosoguanidine mutagenesis, was cultured in 20 ml of CMG-medium at 30° C. with shaking. Cells in the exponential growth phase were harvested, and "competent" cells having the ability of DNA uptake were prepared by the $CaCl_2$-treatment.

Into the competent cell suspension, the DNA obtained was added, and the DNA was incorporated into the cells. After the transformation reaction, the cell suspension was spread on an agar plate containing, 20 g glucose, 10 g $(NH_4)_2SO_4$, 2.5 g urea, 1 g $KH_2PO_4$, 0.4 g $MgSO_4.7H_2O$, 50 μg biotin, 200 μg thiamine hydrochloride, 0.01 g $FeSO_4.7H_2O$, 0.01 g $MnSO_4.4H_2O$, 3.0 g AEC. HCl and 20 g agar, per liter, (pH was adjusted to 7.0). The plate was incubated at 30° C. After 4 days incubation, all of the colonies, which appeared and exhibited productivity of L-lysine and resistance to AEC, picked up, purified and isolated. Thus, a bacterial sample identified as AJ 11575 (FERM-P 5501) (NRRL B-12418) was obtained.

The transformants obtained were cultured to test their L-lysine productivity. The DNA-donor stain No. 22 and the recipient strain No. 97 were cultured in the same manner for comparison.

The culture medium contained 10 g/dl glucose, 0.5 g/dl urea, 4.5 g/dl $(NH_4)_2SO_4$, 0.1 g/dl $KH_2PO_4$, 0.04 g/dl $MgSO_4.7H_2O$, 10 mg/dl adenine, 10 mg/dl sodium glutamate, 0.1 mg/l thiamine. HCl 0.5 mg/l biotin, 1 mg/dl $FeSO_4.7H_2O$, 10 mg/dl $MnSO_4.4H_2O$ and 5 g/dl $CaCO_3$ (separately sterilized) and the pH was adjusted to 8.0.

Twenty ml batches of the fermentation medium were placed in 500 ml flasks. The media were inoculated with one loopful inoculum of the test microorganisms, and the cultivation was performed at 31° C. for 70 hours.

The amounts of L-lysine in the supernatant of the fermentation broth were determined by micro-biological assay.

TABLE 3

| Microorganisms tested | Amount of L-lysine accumulated (mg/dl) |
|---|---|
| *Corynebacterium glutamicum* No. 22 | 120 |
| *Corynebacterium glutamicum* No. 97 | 12 |
| *Corynebacterium glutamicum* AJ 11575 | 235 |

Having now fully described the invention, it will be apparent to one of ordinary skill in the art that many changes and modifications can be made thereto without departing from the spirit or scope of the invention as set forth herein.

What is claimed as new and is intended to be secured by Letters Patent is:

1. A biologically pure composite plasmid capable of propagating in glutamic acid-producing Corynebacteria, comprising:

(a) a genetic region derived from a plasmid and capable of amplifying foreign genes; characterized by a molecular weight of 3.0±0.1 megadalton and having the following restriction endonuclease-cleavage map:

| Hind | III | 0/100 | Hae | III | 76 |
| Bcl | I | 44 | Ava | I | 86 and 99; and |
| Xba | I | 55 | | | |

(b) a foreign gene fragment.

2. The biologically pure composite plasmid of claim 1, comprising pAM 330.

3. The biologically pure composite plasmid of claim 1, comprising pAM 286.

4. The biologically pure composite plasmid of claim 1, wherein the plasmid is selected from pAM 330 and pAM 286.

5. The biologically pure composite plasmid of claim 1, wherein the said foreign gene fragment is a genomic DNA fragment of Cornyeform glutamic acid-producing bacteria.

* * * * *